United States Patent [19]

Scardera et al.

[11] Patent Number: 4,827,028

[45] Date of Patent: May 2, 1989

[54] ANIONIC SURFACTANTS

[75] Inventors: Michael Scardera, Hamden; Richard M. Mullins, Madison, both of Conn.

[73] Assignee: Olin Corporation, Cheshire, Conn.

[21] Appl. No.: 602,992

[22] Filed: Apr. 23, 1984

[51] Int. Cl.$^4$ ............................................. C07C 59/125
[52] U.S. Cl. ............................... 562/583; 252/174.19; 252/174.21; 252/174.22
[58] Field of Search .................... 562/583; 252/174.19, 252/174.21, 174.22

[56] References Cited

U.S. PATENT DOCUMENTS

| | | | |
|---|---|---|---|
| 3,419,510 | 12/1968 | Hudak | 260/18 |
| 3,983,058 | 9/1976 | Hirooka et al. | 260/29 |
| 4,124,552 | 11/1978 | Koleske | 260/29 |
| 4,207,227 | 6/1980 | von Bonin | 260/60 |
| 4,207,421 | 6/1980 | Scardera et al. | 568/625 |
| 4,250,077 | 2/1981 | von Bonin et al. | 260/37 |
| 4,263,413 | 4/1981 | Gardner et al. | 525/34 |
| 4,317,940 | 3/1982 | Scardera et al. | 568/625 |
| 4,365,024 | 12/1982 | Frentzel | 521/114 |
| 4,460,738 | 7/1984 | Frentzel et al. | 524/591 |
| 4,521,615 | 6/1985 | Frentzel | 528/75 |
| 4,533,485 | 8/1985 | O'Connor et al. | 562/583 |
| 4,533,486 | 8/1985 | Scardera et al. | 562/583 |

OTHER PUBLICATIONS

V. Malatesta and J. C. Scaiano, "Absolute Rate Constants for the Reactions of tert-Butyl with Ethers: Importance of the Stereoelectronic Effect," J. Org. Chem., 1982, 47, pp. 1455–1459.
Literature Search (NHTIS 82-215) carried out by Olin Corporation, Olin Product Data Sheet for Poly-G WS Fluids.
Viking Chemical Company Technical Bulletins for VIKOLOX 11–14, 12 and 16.

*Primary Examiner*—Bruce D. Gray
*Attorney, Agent, or Firm*—William A. Simons

[57] ABSTRACT

Described are anionic surfactants which are made by (1) reacting maleic acid, fumaric acid, itaconic acid or mixtures thereof with at least one selected epoxy-capped poly(oxyalkylated) alcohol in the presence of a peroxytype free radical initiator to form a carboxylic acid group-containing addition product and (2) neutralizing said addition product with a sufficient amount of a neutralizing agent to convert at least a major proportion of said carboxylic acid groups to salt groups. These surfactants exhibit excellent surface activity as well as being highly soluble in caustic solutions.

7 Claims, No Drawings

ANIONIC SURFACTANTS

BACKGROUND OF THE INVENTION

1. Field Of The Invention

The present invention relates to the neutralized addition products of selected unsaturated dicarboxylic acids and selected epoxy-capped poly(oxyalkylated) alcohols and their use as anionic surfactants suitable for use in caustic solutions.

2. Brief Description Of The Prior Art

Caustic-soluble surfactants are used today in a wide variety of industries. They are employed in the metal cleaning industry to remove greases and process fluids from metal finishes. They are also used in the textile field to remove knitting oils and the like from textiles. They are used in emulsion polymerization reactions to aid the dispersion of one or more of the reactants in each other or in a solvent. They are also employed in dairy/food plants and in bottle washing operations, as well as household and other consumer cleaners.

Commonly used caustic-soluble surfactants include anionic alkylated diphenyl oxide disulfonate-type surfactants (e.g. DOWFAX 2A1 and 3B2 made by Dow Chemical Co. of Midland, Mich.); nonionic alkylated glucoside-type surfactants (e.g. TRITON BG-10 made by Rohm & Haas of Philadelphia, Pa.); and carboxylic acid-type surfactants (e.g. TRITON DF-20 also made by Rohm & Haas). While these commercially available surfactants may be suitable for certain applications, they have certain deficiencies which prevent their use in many applications. Ideally, an excellent caustic-soluble surfactant should have very good surface activity and high caustic solubility (e.g. soluble in aqueous solutions containing more than about 10% by weight NaOH) as well as low foaming properties and a relatively low cost.

Separately, reactions of carboxylic acids with polyols in the presence of a free radical initiator are known. For instance, U.S. Pat. No. 4,250,077 (von Bonin et al.) teaches mixing olefinically unsaturated carboxylic acids with many types of polyols and then polymerizing the mixture with a free radical former to produce a graft polymer. The preferred carboxylic acid (and the only acid used in the working examples) is acrylic acid, which homopolymerizes with itself. It should be noted that this reference does not teach the exact mechanism by which this "polymerization" reaction is carried out.

U.S. Pat. No. 4,365,024 (Frentzel) teaches making surfactants suitable for incorporation in polyurethane foams by reacting under free radical polymerization conditions a polyoxyalkylene adduct and unsaturated dibasic esters whose acid moities contain 4 or 5 carbon atoms. The mechanism of this reaction is referred to as grafting, i.e. the reaction product is composed of the polyoxyalkylene adduct backbone to which are attached at intervals "grafts" of the unsaturated diester. See column 4, lines 46-51 of this patent. The patent further states that, "In light of the known inability of unsaturated diesters of the invention to homopolymerize, it is believed that the mechanism of the reaction may involve the addition of single diester units to the polyoxyalkylene backbone". The patent specifically teaches that these surfactants may be used in phenolic resin foams, polyisocyanurate foams and polyurethane foams.

U.S. Pat. No. 4,521,615 (Frentzel) and U.S. Pat No 4,460,738 (Frentzel et al.) teach making carboxylic acid-containing mono- and polyether polyol addition products by reacting maleic acid, fumaric acid, itaconic acid, or mixtures thereof with at least one polyhydroxy-containing monoor polyether compound (e.g. a polyether diol or triol) in the presence of a peroxy free radical initiator. These patent applications also disclose making polyurethane prepolymers and aqueous polyurethane dispersions from these carboxylic acid-containing mon-oand polyether polyol addition products. U.S. Pat. No. 4,533,486 issued Aug. 6, 1985 (O'Connor et al.) teaches making carboxylic acid-containing poly(oxyalkylated) alcohol addition products followed by neutralization of those carboxylic acd groups.

Until the present invention, no one has proposed making surfactants by the free-radical addition of single carboxylic acid units at intervals onto the backbone of an epoxy-capped poly(oxyalkylated) alcohol followed by neutralization of these carboxylic acid groups. It was quite surprising that these carboxylic acid-containing epoxy-capped poly(oxyalkylated) alcohols have particularly useful properties as caustic-soluble surfactants. Individual single neutralized acid sites on the backbone provide adequate sites for providing caustic solubility, yet are short enough so as not to interfere with the surface activity and low-foaming properties of surfactant compositions as a whole.

BRIEF SUMMARY OF THE INVENTION

The present invention is, therefore, directed to an anionic surfactant composition made by the process comprising:

a. forming a carboxylic acid group-containing addition product by reacting, in the presence of a peroxy-type free radical initiator, an ethylenically unsaturated dicarboxylic acid selected from the group consisting of maleic acid, fumaric acid, and mixtures thereof with at least one epoxy-capped poly(oxyalkylated) alcohol having the formulae (A) and (B):

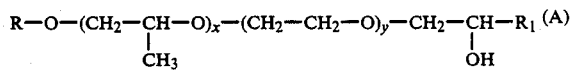

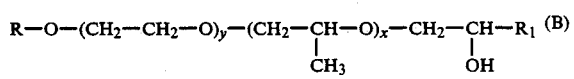

wherein R is a hydrocarbon-containing radical having from 1 to about 8 carbon atoms; $R_1$ is a hydrocarbon-containing radical having from about 6 to about 18 carbon atoms; x is an integer having a value from about 6 to about 40 and y is an integer having a value from about 8 to about 50 with the proviso that the ratio of x:y is from about 2:8 to about 8:2; and said mole ratio of said dicarboxylic acid to said epoxy-capped poly(oxyalkylated) alcohol being from about 1:1 to about 10:1; and b. neutralizing the formed addition product with a sufficient amount of a neutralizing agent to convert at least a major portion of the carboxylic acid groups in said addition product to salt groups.

This neutralization may be carried out when the surfactant composition is prepared or later by adding to an aqueous base or equivalent.

The present invention is also directed to use of these surfactant compositions as surfactants and emulsifiers in aqueous systems, particularly aqueous systems containing more than about 10% by weight of an alkali metal hydroxide (e.g. NaOH).

DETAILED DESCRIPTION

1. Preparation of Carboxylic Acid Group-Containing Addition Product

While the present invention is not to be so limited, this free radical initiated addition reaction is believed to occur by a three-step mechanism, which is illustrated by the following Equations (I) through (X) wherein the poly(oxylated) alcohol employed is represented by A; one of the selected acids is represented by B; and the peroxy-type free radical initiator is presented by ROOR:

Initiation:

$$ROOR \longrightarrow 2RO\bullet \qquad (I)$$

Propagation:

$$A + RO\bullet \longrightarrow A\bullet + ROH \qquad (II)$$

$$A\bullet + B \longrightarrow A-B\bullet \qquad (III)$$

-continued $$A-B\bullet + A \longrightarrow A-B + A\bullet \qquad (IV)$$

$$A-B\bullet + ROOR \longrightarrow A-B-OR + RO\bullet \qquad (V)$$

$$A-B\bullet + ROH \longrightarrow A-B + RO\bullet \qquad (VI)$$

Termination:

$$2RO\bullet \longrightarrow ROOR \qquad (VII)$$

$$A\bullet + A\bullet \longrightarrow A-A \qquad (VIII)$$

$$AB\bullet + A\bullet \longrightarrow A-B-A \qquad (IX)$$

$$AB\bullet + AB\bullet \longrightarrow ABBA \qquad (X)$$

In the case where the epoxy-capped poly(oxalkylated) alcohol (A) is $C_4H_{10}O \cdot 8$ moles oxypropyl $\cdot 8$ moles oxyethyl $\cdot$ 1,2-epoxydodecane and the acid (B) is either maleic acid [cis-HOOCCH=CHCOOH] or fumaric acid (trans-HOOCCH=CHCOOH], Equations (II), (III) and (IV) would be written respectively as Equations (IIa), (IIIa) and (IVa) and as shown below:

$$C_4H_9O-(CH_2-\underset{CH_3}{\underset{|}{CH}}-O)_8-(CH_2-CH_2-O)_8-CH_2-\underset{OH}{\underset{|}{CH}}-C_{10}H_{21} + RO\bullet \longrightarrow \qquad (IIa)$$

$$C_4H_9O-CH_2-\underset{\bullet}{\underset{|}{\overset{CH_3}{\overset{|}{C}}}}-O-(CH_2-\underset{|}{\overset{CH_3}{\overset{|}{CH}}}-O)_7-(CH_2-CH_2-O)_8-CH_2-\underset{OH}{\underset{|}{CH}}-C_{10}H_{21} + ROH$$

$$C_4H_9O-CH_2-\underset{\bullet}{\underset{|}{\overset{CH_3}{\overset{|}{C}}}}-O-(CH_2-\underset{|}{\overset{CH_3}{\overset{|}{CH}}}-O)_7-(CH_2-CH_2-O)_8-CH_2-\underset{OH}{\underset{|}{CH}}-C_{10}H_{21} + \qquad (IIIa)$$

$$HO\overset{O}{\overset{\|}{C}}-CH=CH-\overset{O}{\overset{\|}{C}}OH \longrightarrow$$

$$C_4H_9O-CH_2-\underset{\underset{\underset{HO}{|}}{\underset{O=C}{|}}{\underset{HC-CH}{|}}}{\overset{CH_3}{\overset{|}{C}}}-O-(CH_2-\overset{CH_3}{\overset{|}{CH}}-O)_7-(CH_2-CH_2-O)_8-CH_2-\underset{OH}{\underset{|}{CH}}-C_{10}H_{21}$$

$$C_4H_9O-CH_2-\underset{\underset{\underset{HO}{|}}{\underset{O=C}{|}}{\underset{HC-CH}{|}}}{\overset{CH_3}{\overset{|}{C}}}-O-(CH_2-\overset{CH_3}{\overset{|}{CH}}-O)_7-(CH_2-CH_2-O)_8-CH_2-\underset{OH}{\underset{|}{CH}}-C_{10}H_{21} + \qquad (IVa)$$

$$C_4H_9O-(CH_2-\overset{CH_3}{\overset{|}{CH}}-O)_8-(CH_2-CH_2-O)_8-CH_2-\underset{OH}{\underset{|}{CH}}-C_{10}H_{21} \longrightarrow$$

-continued

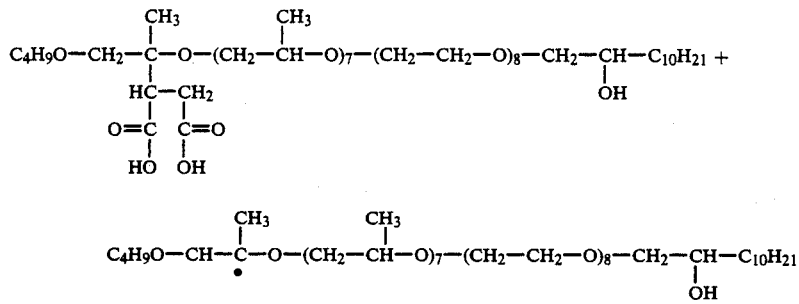

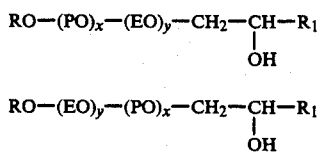

As can be seen in Equation (IIIa), above, the carboxylic acid replaces a hydrogen atom on a carbon adjacent to an oxygen atom in an either linkage (C—O—C). With $C_4H_9$. 8PO .8EO. 1,2-epoxydode cane as the epoxy-capped poly(oxyalkylated) alcohol, there are a total of 32 sites where it is believed the acid groups may replace a hydrogen. These sites are the carbon atoms adjacent to an ether-oxygen. Thus, it is possible in theory that individual carboxylic acid groups may attach to all 32 sites on this particular poly(oxyalkylated) alcohol. In practice, it is believed that steric effects will prevent the attachment of that many acid groups as close to each other on the alcohol.

Maleic acid and fumaric acid and are the only known ethylenically unsaturated dicarboxylic acids that are suitable for this invention because they do not homopolymerize. Free radical addition reactions with them are completed by removal of a hydrogen from another polyol [see Equation (IV) above] or from another hydrogen atom source. Furthermore, it has been found that these carboxylic acids [when reacted to epoxy-capped poly(oxyalkylated) alcohols according to the present invention] are particularly suitable for making caustic-soluble surfactants.

Suitable epoxy-capped poly(oxyalkylated) alcohols for the present invention include the following types:

$$RO-(PO)_x-(EO)_y-CH_2-\underset{\underset{OH}{|}}{CH}-R_1$$

$$RO-(EO)_y-(PO)_x-CH_2-\underset{\underset{OH}{|}}{CH}-R_1$$

wherein x and y are as defined above and R and $R_1$ are as defined above and PO and EO stand for propylene oxide and ethylene oxide groups, respectively. It should be noted that the EO and PO groups may be added to the alcohol by random condensation rather than by block condensation and the present invention also encompasses said random condensation within the defined limit of x and y. Preferably, R is a linear, aliphatic hydrocarbon radical having an average of from about 1 to about 8 carbon atoms. Preferably, $R_1$ is a linear, aliphatic hydrocarbon radical having an average of from about 10 to about 16 carbon atoms. Preferably, x is an integer having a value from about 6 to about 20. Preferably, y is an integer having a value from about 10 to about 25. The ether linkages in these epoxy-capped poly(oxyalkylated) alcohols are needed to form the formation of free radicals on the adjacent carbons. See V. Malatesta and J. C. Scaiano, "Absolute Rate Constants for the Reaction of tert-Butoxyl with Ethers: Importance of Stereoelectronic Effect", *J. Org. Chem.*, 1982, 47, pages 1455–1459.

The epoxy-capped poly(oxyalkylated) alcohol precursors shown in Equations (A) and (B) may be made be condensing the corresponding poly(oxyalkylated) alcohols with a suitable epoxide. Generally, these poly(oxyalkylated) alcohols may be made by condensing an aliphatic alcohol, or mixture of alcohols, of desired average chain length with ethylene oxide followed by capping this condensation product with propylene oxide or vice versa. Alternatively, this condensation may be carried out with a mixture of EO and PO to form a random product. The moles of EO and PO employed per mole of alcohol will preferably fall within the ranges for x and y as given above. The methods used for condensing and capping may be any of the well-known methods described in the art. Preferably, these reactions occur at elevated temperatures in the range of about 120° C. to about 180° C. (more preferably from about 140° C.-170° C.). It is also preferred to carry out such reactions in the presence of an effective amount (e.g. about 0.005% to 1% by weight of the alcohol weight) of a suitable alkaline catalyst(s) such as salts or hydroxides of the alkali metals or alkaline with metals. The preferred catalyst is KOH. Suitable poly(oxylalkylated) alcohols include POLY-G ® WS polyalkylene glycol derivatives made by Olin Corporation of Stamford, Conn.

Suitable epoxy compounds useful for making the epoxy-capped poly(oxyalkylated) alcohol precursors of the present invention include any 1,2-epoxyalkanes, or mixtures thereof, having a hydrocarbon chain containing an average of about 6 to about 18 carbon atoms. Preferably, the 1,2-epoxyalkane has a linear, aliphatic hydrocarbon chain containing from about 10 to about 14 carbon atoms. These 1,2-epoxyalkane compounds are commercially available from the Viking Chemical Company of Minneapolis, Minn. under the product names VIKOLOX 11-14, VIKOLOX 12 and VIKOLOX 16.

It should be noted that not all free radical initiators may be used for this reaction. Only peroxy-type free radical initiator may be employed. Other types of initiators are not suitable for this reaction. Typical peroxy-type free radical initiators include hydrogen peroxide and organo peroxides and hydroperoxides such as dibenzoyl peroxide, acetyl peroxide, benzoyl hydroperoxide, t-butyl hydroperoxide, di-t-butyl peroxide, lauroyl peroxide, butyryl peroxide, diisopropylbenzene hydroperoxide, cumene hydroperoxide, paramenthane hydroperoxide, diacetyl peroxide, dialphacumyl peroxide, dipropyl peroxide, diisopropyl peroxide, isopropyl-t-butyl peroxide, butyl-t-butyl peroxide, dilauroyl peroxide, difuroyl peroxide, ditriphenylmethyl peroxide, bis(p-methoxy-benzoyl) peroxide, p-monomethoxybenzoyl peroxide, rubrene peroxide, ascaridol, t-butyl peroxybenzoate, diethyl peroxyterephthalate, propyl hydroperoxide, isopropyl hydroperoxide, n-butyl hydroperoxide, t-butyl hydroperoxide, cyclohexyl hydroperoxide, trans-Decalin hydroperoxide, alpha-methylbenzyl hydroperoxide, alpha-methyl-alpha-ethyl benzyl hydroperoxide, Tetralin hydroperoxide, triphenylmethyl hydroperoxide, diphenyl-methyl hydroperoxide, 2,5-di-methyl- 2,5-bis(2-ethyl hexanoyl peroxy)hexane, 1,1-bis(t-butyl-peroxy) cyclohexane and t-butyl perbenzoate.

As stated above, the mole ratio of the unsaturated dicarboxylic acid to the epoxy-capped poly(oxyalkylated) alcohol(s) employed should be from about 1:1 to about 10:1. When less than about 1 mole of the acid is used per about 1 mole of the poly(oxyalkylated) alcohol, the character of the resulting addition product is hardly changed and this reaction is meaningless for most applications. When more than about 10 moles of the acid is employed per mole of the poly(oxyalkylated) alcohol, there is a good chance that a significant portion of the acid will not react onto the alcohol because of absence of sufficient reactive sites. Preferably, this mole ratio is from about 2:1 to about 8:1.

Besides the selected reactants, peroxy-type initiators and weight ratios mentioned above, the other reaction conditions of this step are not critical to the present invention and the present process should not be limited to any particular conditions. It is preferred to carry out this reaction at a temperature from about 25° C. to about 150° C. More preferably, the reaction temperature may be in the range from about 80° C. to about 130° C. The reaction temperature should be high enough to activate the peroxy-type free radical initiator for this reaction. In some cases, it may be desirable to add a free radical accelerator such as a Redox catalyst to speed up the reaction. The reaction time will depend mainly upon the reaction temperature used and suitable reaction times will range from about 30 minutes to 24 hours. The reaction may be monitored by following the disappearance of the maleic or fumaric acid in the reaction mixture with conventional analysis techniques.

Generally, this reaction may be carried out without a solvent. However, in some cases, it may be desirable to employ a solvent. For example, if a very viscous poly(oxyalkylated) alcohol is employed, it may be desirable to thin the reaction mixture with water or another solvent to facilitate the reaction.

Furthermore, super- or sub-atmospheric reaction pressure is not necessary for the present reaction. Atmospheric pressure is preferred in order to avoid the expense of special reaction vessels.

The free radica initiated reaction of this invention may be conducted under conditions known to be suitable for free radical polymerizations. The reaction is advantageously carried out by mixing the reactants, initiator(s), and optionally with a free radical accelerator(s) and solvent, at temperatures from about 25° C. to about 150° C. with an inert atmosphere (e.g. under a nitrogen blanket) until the reaction is complete. The initiator(s) and optional catalyst(s) and solvent may be added at the beginning of the reaction or may be added portionwise at intervals during the course of reaction. Likewise, the unsaturated acid reactant(s) and the epoxy-capped poly(oxyalkylated) alcohol(s) reactants may be brought together at the beginning of the reaction or may be combined in increments as the reaction proceeds.

The adducts produced by this reaction are generally water-insoluble, but they may be converted into water-dispersible form by reaction with a conventional neutralization agent (e.g. an inorganic or organic base) which converts some or all of the carboxylic acids groups into ionic groups according to well-known methods.

2. Neutralization Of The Addition Product

As stated above, the formed addition product is neutralized in accordance with this invention in order to convert at least a major portion (i.e. at least 50%) of the carboxylic acid groups on the addition product.

Any conventional neutralizing agent may be employed. Preferred agents include water-soluble tertiary amines (e.g. triethanolamine), alkali metal hydroxides and mixtures thereof. The most preferred neutralization agents are sodium hydroxide and potassium hydroxide.

The amount of neutralization agent added is preferably sufficient to convert about 70% of the carboxylic acid groups in the addition product to salt groups (e.g. $-COO^-Na^+$). The presence of these salt groups allows the composition to be caustic- and water-soluble. It should be noted that the neutralization agent may also be a caustic-containing processing bath or the like in which the surfactant is to be used. In this latter case, it may be desirable to merely add the unneutralized (or free-acid) adduct of the present invention and allow the neutralization to take place in-situ.

Basically, the surfactant compositions of the present invention consist of five components - an alcohol, ethylene oxide, propylene oxide, epoxy cap and neutralized carboxylic acid groups. The long chain epoxy cap serves as a hydrophobic, oil-soluble portion of the surfactant. The short chain alcohol and ethylene oxide group form the hydrophilic water-soluble elements of the surfactant. However, the ethylene oxide group is susceptible to degradation in caustic and other alkaline solutions. Such instability may render such surfactants incompatible in various compositions used in industrial household and institutional applications. To improve the alkali stability, the propylene oxide groups are also present. These PO groups also provide low foaming characteristics. The neutralized carboxylic acid groups provide the compositions with aqueous and caustic solubility. If biodegradable characteristics are also desired, then it is preferred that an aliphatic alcohol and aliphatic epoxy cap both be substantially linear with essentially no branching. This linearity is vital to the biodegradability of the surfactant product. Accordingly, the surfactant compositions of the present invention, therefore, may be biodegradable, both water and caustic soluble, have low to moderate foaming, while being stable with dry caustic.

3. Use Of Compositions As Surfactants

The advantageous properties of the surfactant compositions of the present invention may be useful in a variety of applications, in particular in metal cleaning formulations, as wetting, washing and dispersing agents in the textile, leather, paper, paint, pharmaceutical and cosmetic industries, as well as for household applications. Specifically, the anionic surfactants of the present invention may be used as surface active agents or emulsifiers in aqueous mixture (e.g. solutions, suspensions and the like) containing at least about 10%, more preferably from about 15% to about 35%, by weight of an alkali metal hydroxide (e.g. NaOH and KOH).

The following examples are provided to further illustrate the invention. All parts and percentages are by weight unless otherwise specified.

EXAMPLE 1

A 500 ml 3-necked round bottom flask containing a magnetic stirrer was fitted with a thermometer, nitrogen inlet dropping funnel, and air condenser. POLY-G ® WS-260 ①, 100 g (0.1 mole), and 0.4 g potassium hydroxide were placed in the flask. The contents of the flask were heated to 150°-155° C. with stirring. Via the addition funnel, 18.6 g (0.1 mole) 1,2-epoxydodecane was added dropwise over a 75 minute period and post-reacted for an additional 30 minutes. The reaction mixture was cooled and the product, POLY-G ® WS-260 expoxydodecane adduct, was weighed (118.6 g). Half of the product weight, 59.25 g (0.05 mole) was recharged to the 500 ml reaction flask and 23.2 g (0.2 moles) fumaric acid was added. The reaction mixture was heated to 135°-140° C. and 1 ½ mls of di-tert-butyl peroxide was added. After heating and stirring for 3 hours an additional 1 ½ mls of di-tert-butyl peroxide was added, and the reaction continued for an additional 7 hours. The product was cooled, removed from the flask, and weighed (82.2 g). A total of 74.5 g of this product was neutralized to a pH of 7 with 9 g sodium hydroxide in 57 g distilled water. The product consisted of a 59.4% solution of POLY-G ® WS-260/epoxydodecane/4 moles sodium fumarate adduct. A 2% by weight solution of this product was soluble in a solution of 25% by weight sodium hydroxide.

① A 50/50 weight ratio random ethylene oxide-propylene oxide adduct on butanol, molecular weight 1,000.

EXAMPLE 2

Employing the same equipment described in Example 1, 50 g (0.05 mole) POLY-G ® WS-260 and 0.2 g potassium hydroxide were placed in the 500 ml flask. After heating the contents to 150°-155° C. with stirring, 9.3 g (0.05 mole) 1,2-epoxydodecane was added dropwise over a 65 minute period and post-reacted for an additional 90 minutes. The temperature of the reaction mixture was reduced to 120° C. and 1.5 g of the adduct was removed for analytical purposes. To the remainder of the product 11.6 g (0.1 mole) fumaric acid and 1.5 ml of di-tert-butyl peroxide was added. The reaction mixture was heated at 120°-130° C. for 27 hours. The product was cooled, removed from the flask, and weighed (68.7 g). A total of 66.5 g of this solution was neutralized to a pH of 7 with 8.25 g 50% sodium hydroxide solution and 58 g distilled water. The product consisted of a 50% solution of POLY-G ® WS-260/epoxydodecane/2 moles sodium fumarate adduct. A 2% by weight solution of this product was soluble in a solution of 20% by weight sodium hydroxide.

EXAMPLE 3

Equipment and procedure are the same as described in Example 1. POLY-G ® WS-660 ②, 90.98 (0.05 mole), was substituted for the POLY-G ® WS-260 and reacted with 9.2 g (0.05 mole) 1,2-epoxydodecane with 0.04 g potassium hydroxide as the catalyst. Upon completion of the addition, 23.2 g (0.2 moles) fumaric acid was added employing 3 ml di-tert-butyl peroxide as the free radical initiator. After heating at 130°-135° C. for 24 hours, the reaction mixture was cooled to ambient temperature, removed from the reaction flask, and weighed (124.4 g). The product was neutralized to a pH of 7 with 9.5 g sodium hydroxide in 115 mls distilled water. The product consisted of a 50% solution of POLY-G ® WS-660/epoxydodecane/4 moles sodium fumarate adduct. A 2% by weight solution of this product was soluble in a solution of 7% by weight sodium hydroxide.

② A 50/50 by weight random ethylene oxide-propylene oxide adduct on butanol, molecular weight 1,800.

PHYSICAL AND SURFACE PROPERTIES DETERMINATION

EXAMPLES 1, 2, AND 3

To illustrate the favorable surfactant properties of the sodium fumarate products of Examples 1, 2, and 3 the following tests were conducted, with results listed in Table A.

"Cloud Point" is an indication of water solubility. A 1% aqueous solution of the surfactant is heated until a point is reached where the surfactant begins to separate out, causing the solution to become turbid or cloudy. This is the "Cloud Point".

"Surface Tension" is the force related to the intermolecular attraction at a liquid-air interface. This property indicates the tendency of a liquid to spread or wet solid surfaces. (Per ASTM D 1331-56)

"Interfacial Tension" is the force related to the intermolecular attraction of a liquid-liquid or liquid-solid interface. This property is indicative of effective emulsification; bubble, film and foam formation and behavior; cleaning of fabrics; ore flotation; adhesives; and the like. (Per ASTM D 1331-56)

"Draves Wetting Time" denotes the time required to wet a 5 g cotton skein in an aqueous solution of surfactant. This property is important to textile processing utility. (Per AATCC Method 17-1952)

"Ross-Miles Foam Height" is a measure of the foam height generated initially and remaining after 5 minutes in a surfactant solution. This test indicates both foam tendency (low-moderate-high) and foam stability. (Per ASTM Method D 1173-53)

As Table A illustrates, the surfactant product of the present invention features good water solubility, as well as favorable wetting and emulsification capability. The Ross-Miles test results show that the surfactant achieves moderate to high initial foaming and adequately maintains such foam height. Solubility with alkali also is demonstrated.

TABLE A

| | SURFACE PROPERTIES | | |
|---|---|---|---|
| Example | 1 | 2 | 3 |
| Cloud Point, 1% °C. | 98 | 45 | 98 |
| NaOH Solubility, * (%) | 25 | 20 | 7 |
| Surface Tension, dynes/cm | | | |
| 0.001 | 47.3 | 43.9 | 52.1 |
| 0.01 | 37.2 | 35.4 | 41.7 |
| 0.1 | 33.0 | 32.4 | 29.6 |
| Interfacial Tension, dynes/cm | | | |
| 0.001 | 20.5 | 18.3 | 25.5 |
| 0.01 | 11.6 | 9.3 | 14.9 |
| 0.1 | 7.9 | 6.6 | 7.7 |
| Draves Wetting Time, secs. @ 25° C. | | | |
| 0.10 | 43 | 22 | 65 |
| 0.25 | 20 | 12 | 24 |
| Ross-Miles Foam Height, mm Initial/after 5 mins. | | | |

TABLE A-continued

| | SURFACE PROPERTIES | | |
|---|---|---|---|
| Example | 1 | 2 | 3 |
| @ 25° C. | | | |
| 0.25 | 80/25 | 75/30 | 100/95 |
| 0.50 | 95/30 | 80/40 | 110/100 |

\* Solubility of 1% Surfactant in percentage of aqueous NaOH solution.

What is claimed is:

1. A surfactant composition made by the process comprising:
   a. forming a carboxylic acid group-containing addition product by reacting, in the presence of a peroxy-type free radical initiator, an ethylenically unsaturated dicarboxylic acid selected from the group consisting of maleic acid, fumeric acid and mixtures thereof, with at least one epoxy-capped poly(oxyalkylated) alcohol having the formulae (A) and (B):

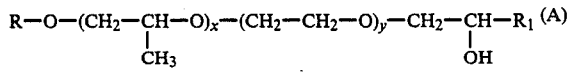

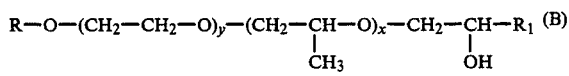

wherein R is an aliphatic hydrocarbon-containing radical having from 1 to about 8 carbon atoms; $R_1$ is an aliphatic hydrocarbon- containing radical having from about 6 to about 18 carbon atoms; x is an integer having a value from about 6 to about 40 and y is an integer having a value from about 8 to about 50 with the proviso that the ratio of x:y is from about 2:8 to about 8:2; and said mole ratio of said dicarboxylic acid to said epoxy-capped poly-(oxyalkylated) alcohol being from about 1:1 to about 10:1; and
   b. neutralizing said addition product with a sufficient amount of a neutralizing agent to convert at least a major portion of said carboxylic acid groups to salt groups.

2. A surfactant composition made by the process comprising:
   a. forming acarboxylic acid group-containing addition product by reacting, in the presence of a peroxy-type free radical initiator, an ethylenically unsaturated dicarboxylic acid selected from the group consisting of maleic acid, fumaric acid and mixtures thereof, with at least one epoxy-capped poly(oxyalkylated) alcohol having the formulae (A) and (B):

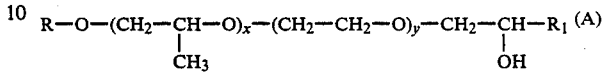

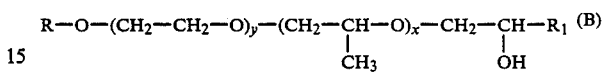

wherein R is an aliphatic hydrocarbon-containing radical having from 1 to about 8 carbon atoms; $R_1$ is an aliphatic hydrocarbon-containing radical having from about 6 to about 18 carbon atoms; x is an integer having a value from about 6 to about 40 and y is an integer having a value from about 8 to about 50 with the proviso that the ratio of x:y is from about 2:8 to about 8:2; and said mole ratio of said dicarboxylic acid to said epoxy-capped poly(oxyalkylated) alcohol being from about 1:1 to about 10:1.

3. The surfactant composition of claim 1 wherein R is a linear, aliphatic hydrocarbon radical having an average of from about 1 to about 8 carbon atoms.

4. The surfactant composition of claim 1 wherein $R_1$ is a linear, aliphatic hydrocarbon radical having an average of from about 10 to about 16 carbon atoms.

5. The surfactant composition of claim 1 wherein the mole ratio of said dicarboxylic acid to said poly(oxyalkylated) alcohol is from about 2:1 to about 8:1.

6. The surfactant composition of claim 1 wherein said addition product is neutralized with a sufficient amount of a neutralizing agent to convert at least 70% of carboxylic acid groups to salt groups.

7. The process of using a surfactant in an aqueous solution containing at least about 10% by weight of an alkali metal hydroxide, wherein said surfactant is a surfactant composition of claim 1.

* * * * *